US008709740B2

(12) United States Patent
Martin et al.

(10) Patent No.: US 8,709,740 B2
(45) Date of Patent: Apr. 29, 2014

(54) CONTROL OF PROTEIN ACTIVITY USING A CONDUCTING POLYMER

(75) Inventors: Brett D. Martin, Washington, DC (US); Luminita M. Velea, Herndon, VA (US); Banahalli Ratna, Woodbridge, VA (US); Bruce P. Gaber, Bethesda, MD (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 683 days.

(21) Appl. No.: 11/203,575

(22) Filed: Aug. 11, 2005

(65) Prior Publication Data

US 2007/0037240 A1 Feb. 15, 2007

(51) Int. Cl.
*C12Q 1/34* (2006.01)
*C12N 13/00* (2006.01)
*C12N 11/00* (2006.01)

(52) U.S. Cl.
USPC .......................... 435/18; 435/173.1; 435/174

(58) Field of Classification Search
None
See application file for complete search history.

(56) References Cited

U.S. PATENT DOCUMENTS

| | | | |
|---|---|---|---|
| 5,156,810 A * | 10/1992 | Ribi | 422/82.01 |
| 5,210,217 A | 5/1993 | Albarella et al. | |
| 5,403,451 A * | 4/1995 | Riviello et al. | 205/777.5 |
| 5,422,246 A | 6/1995 | Koopal et al. | |
| 5,766,934 A | 6/1998 | Guiseppi-Elie | |
| 5,843,741 A | 12/1998 | Wong et al. | |
| 6,395,527 B1 * | 5/2002 | Beraud et al. | 435/195 |
| 6,660,484 B2 | 12/2003 | Charych et al. | |
| 6,696,575 B2 | 2/2004 | Schmidt et al. | |

OTHER PUBLICATIONS

Hess H et al (2001) Molecular shuttles based on motor proteins: active transport in synthetic environments. Rev in Mol Biotechnol, vol. 82, pp. 67-85.*
Ha Y-H et al (Jun. 2004) Towards a transparent, highly conductive poly(3,4-ethylenedioxythiophene). Advanced Functional Materials, vol. 14, No. 6, pp. 615-622.*
Kros et al., Poly(3,4-ethylenedioxythiophene)-Based Copolymers for Biosensor Applications., Journal of Polymer Science Part A: Polymer Chemistry, 2002, vol. 40, 738-747.*
Martin et al., Reversible control of kinesin activity and microtubule gliding sppeds by switching the doping states of a conducting polymer support., 2007, vol. 18, pp. 1-7.*
Fitzgerald, Division of Mathematics and Science, Chemistry Department, 2005, Sponsored Research report of "New Approaches to Organic Materials for Photovoltaic Applications", pp. 1-41.*
Miyashita et al., Electrochemcal Properties and Photoelectrochemical Response of Vacuum-deposited Poly (p-phenylene., Polymers for Advanced Technilogies, 1996, vol. 7, pp. 657-661.*

(Continued)

*Primary Examiner* — Alexander Kim
(74) *Attorney, Agent, or Firm* — US Naval Research Laboratory; Joseph T. Grunkemeyer

(57) ABSTRACT

A device having a substrate and an enzyme attached to the substrate. The substrate has a polymeric surface having at least two conductivity states. A minimum voltage that does not cause a redox reaction in the enzyme may be applied to the polymeric surface to change the conductivity state of the surface. A method of controlling enzyme activity by providing the above substrate with polymeric surface, attaching an enzyme to the substrate, and altering the conductivity state of the polymeric surface. Changing the conductivity of the polymer can change the activity of the enzyme.

11 Claims, 5 Drawing Sheets

(56) References Cited

OTHER PUBLICATIONS

Pandey et al., A New Conducting Polymer-coated biosensor., J. Chem. Soc., Faraday Trans, 1988, vol. 84, pp. 2259-2265).*

Forzani et al., A Conducting Polymer Nanojunction Sensor for Glucoes Detection., Polymer Chemistry, 2002, vol. 40, pp. 738-747.*

McQuade et al., Conjugated Polymer-Based Chemical Sensors, Chem. Rev., 2000, vol. 100, pp. 2537-2574.*

Wallace et al. Conductive Electroactive Polymers, Intelligent Materials Systems, CRC Press (2003), pp. $1^{st}$ to $230^{th}$.*

Berliner et al., Microtubule Movement by a Biotinated Kinesin Bound to a Streptavidin-coated Surface., The Journal of Biological Chemistry (1994), vol. 269, pp. 8610-8615.*

Liu et al, "Enzymatic activity of Glucose Oxidas Covalently Wired via Viologen to Electrically Conductive Polypyrrole Films", Elsevier, 2000, vol. 19, pp. 823-834.

Ryder et al, "Role of Conducting Polymeric Interfaces in Promoting Biological Electron Transfer", Elsevier, 1997, vol. 12, No. 8, pp. 721-727.

Liu et al, "Control of a Biomolecular Motor-Powered Nanodevice with an Engineered Chemical Switch", Nature, Nov. 2002, Vo. 1, pp. 173-177.

Schmidt et al, "Electrical Stimulation Alters Protein Adsorption and Nerve Cell Interactions with Electrically Conducting Biomaterials", Elsevier, 2001, vol. 22, pp. 1055-1064.

Lahann e al, "A Reversibly Switching Surface", Science Magazine, Jan. 2003, vol. 299, pp. 371-374.

Servagent-Noinville et al, "Conformational Changes of Bovine Serum Albumin Induced by Adsorption on Different Clay Surfaces: FTIR Analysis",Idealibrary, 2000, vol. 221, pp.

Baron et al, "Chymotrypsin Adsorption on Montmorillonite: Enzymatic Activity ans Kinetis FTIR Structural Analysis", Idealibrary, 1999, vol. 214, pp. 319-332.

Uchiyama et al, "Electrical Control of Urease Activity Immobilized to the Conducting Polymer on the Carbon Felt Elecrode", Electroanalysis, 2002, vol. 14, No. 23, pp. 1-4.

Marvin et al, "The Rational Design of Allosteric Interactions in a Monomeric Protein and its Applications to the Constructiom of Biosensors", Natl. Acad. Sci, USA, Apr. 1997, Vol.

Bio-Molecular Motors Conference, Feb. 1, 2005.

* cited by examiner

ATP=S $$E+S \underset{k_{-1}}{\overset{k_1}{\rightleftharpoons}} ES \xrightarrow{K_{cat}} E+P \qquad K_{cat} = \frac{SPEED_{max}}{D_{step}} \qquad K_m = \frac{[E][S]}{[ES]}$$

CONTROL OF PROTEIN ACTIVITY USING A CONDUCTING POLYMER

BACKGROUND OF THE INVENTION

1. Field of the Invention

The invention generally relates to controlling the activity of a protein on a substrate.

2. Description of the Related Art

ATPases such as kinesin are central to several life processes. These proteins are found in organisms representing all of the major eukaryotic kingdoms. The common bond among the kinesins is a highly conserved "motor" domain, ~350 amino acids long, which contains binding sites for ATP and cytoskeletal microtubules. Kinesins are intimately associated with the microtubules, and in concert with them drive cell division processes, mediate intracellular transport of organelles, chromosomes, and RNA. In vivo, kinesin activity is moderated reversibly and irreversibly via enzymatic phosphorylation of specific amino acid residues and chemical inhibitors.

Kinesin is allosteric, that is, a ligand binding event in a given region of the protein can cause a conformation change in a distant region. If the conformationally-affected region contains the catalytic site, the enzyme may exhibit an increased or decreased ability to bind and/or transform substrate. (Marvin et al., "The rational design of allosteric interactions in a monomeric protein and its applications to the construction of biosensors", *Proc. Natl. Acad. Sci. USA, 94*, 4366(1997). All referenced publications and patent documents are incorporated herein by reference.) In the literature there is one example of an allosteric "switch" artificially introduced into F1-ATPase (closely related to kinesin) via protein engineering. In this example, the "switch" is a pocket that binds a $Zn^{++}$ ion. When the ion is bound, the ATPase loses roughly 75% of its activity. The "switch" is, however, not reversible. When the ion is removed via chelation, the ATPase activity is partially, but not fully, restored (Liu et al., "Control of a biomolecular motor-powered nanodevice with an engineered chemical switch", *Nature Mat., 1*, 173 (2002)). The catalytic activity of redox enzymes (enzymes that use electrons as a substrate) has been controlled using conducting polymer surfaces (Ryder et al., "Role of conducting polymeric interfaces in promoting biological electron transfer", *Biosensors & Bioelectronics, 12*, 721 (1997); Liu et al., "Enzymatic activity of glucose oxidase covalently wired via viologen to electrically conductive polypyrrole films", *Biosensors & Bioelectronics, 19(8)*, 823-834 (2004)). In these cases, the polymer merely served as a conduit for the electron substrate, with higher currents allowing an increased enzyme activity because of the increased number of electrons available. The catalytic activity of urease (not a redox enzyme) reportedly has been controlled using a conducting polymer surface. In this case, an electron is able to reduce a disulfide bond in the active site, generate a catalytic thiol, and thus activate the enzyme (Uchiyama et al., "Electrical control of urease activity immobilized to the conducting polymer on the carbon felt electrode", *Electroanalysis, 14*, 1644 (2002)).

Protein structural changes can also be caused by the charged surfaces of minerals such as montmorillonite and other clays. For example, bovine serum albumin and chymotrypsin undergo significant changes in folding/conformation (shown by FTIR), and catalytic activity as they adsorb to these inorganic surfaces.

There have been disclosures concerning the combination of conducting polymers/surfaces and proteins describing the conducting surface as a conduit for information transduction (such as detection of a binding event), or for electron supply for redox proteins (Koopal et al., U.S. Pat. No. 5,422,246; Guiseppe-Elie, U.S. Pat. No. 5,766,934; Albarella et al., U.S. Pat. No. 5,210,217; Charych et al., U.S. Pat. No. 6,660,484).

SUMMARY OF THE INVENTION

The invention comprises a device comprising a substrate and an enzyme attached to the substrate. The substrate comprises a polymeric surface having at least two conductivity states. A minimum voltage that does not cause a redox reaction in the enzyme may be applied to the polymeric surface to change the conductivity state of the surface.

The invention further comprises a method of controlling enzyme activity comprising providing the above substrate with polymeric surface, attaching an enzyme to the substrate, and altering the conductivity state of the polymeric surface.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

Figure 1:
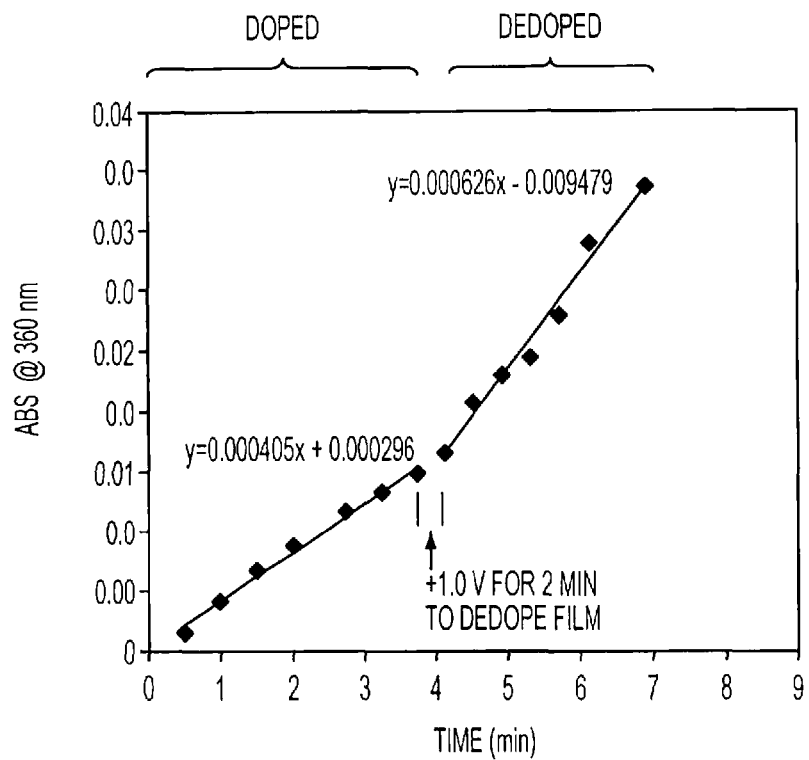
FIG. 1 shows a plot of ATP consumption for both doped and dedoped substrates.

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Disclosed is, for example, a method of controlling the catalytic activity of an enzyme by using a hydroxylated, pi-conjugated conducting polymer as a support. When the enzyme-supporting polymer is in its doped form, i.e. when in its polycationic, conducting state, the ATPase activity of kinesin from *Drosophila* sp. (K401-BCCP-His6) is ca. 44% of the maximum achievable. When the polymer is electrochemically cycled to its dedoped, neutral, semiconducting state the kinesin activity increases to ca. 70% of the maximum achievable. The doping-dedoping cycle may be repeated indefinitely, thus the enzyme activity can be altered in a reversible manner. Michaelis-Menten kinetic studies show that the con-
} ducting polymer may exert its moderating effect on the enzyme by acting on the enzyme-ATP/ADP complex, not on the free enzyme itself, and not on the ATP substrate alone. This suggests that kinesin undergoes a conformation change upon substrate binding that makes it susceptible to influences from the conducting polymer support, such as ion-pairing (doped polymer state) or hydrophobic interactions (dedoped polymer state). The hydroxyls (hydroxymethyl moieties) may play a role in enabling the pi-conjugated polymer moieties to exert their switching effect on the enzyme. The enzyme activity was monitored by measuring phosphate release rates and by measuring the gliding speed of kinesin-driven fluorescent protein microtubules (MTs).

Among the numerous molecular designs for conducting polymers, the development of those based on a thienyl diether (3,4-ethylenedioxythiophene, or EDOT) has shown substantial promise because of their very high conductivities and high transparency in the visible range. The EDOT monomer may be spin-cast onto a glass or plastic substrate and an oxidative polymerization performed, forming a thin conducting film. Conductivities of ~700 S/cm with a 75% film transparency have been obtained. The approach can be extended to the polymerization of a hydroxymethyl-substituted EDOT, 2-hydroxymethyl thieno[3,4-b]-1,4-dioxane (OH-EDOT, also possibly named 2,3-dihydrothieno [3,4-b][1,4]dioxin-2-yl methanol). The resulting poly(OH-EDOT) can have conductivities of as high as 900 S/cm with an 80% film transparency. When the film is immersed in an electrolyte and an electrical bias of −0.45 V (relative to Ag/AgCl) is applied, the film is switched from its cationic, conducting "doped" state to its neutral, semiconducting "dedoped" state. This switching process is fully reversible. This was the conducting polymer used for the studies with protein described below.

A possible benefit of the invention is that it can provide a simple method for the reversible control of protein activity. In the specific example given, the use of the conducting polymer for kinesin activity moderation and, ultimately, microtubule speed control will allow a great sophistication in device designs.

It may be possible to link the kinesin activity to that of yet other proteins. In this way the kinesin-conducting polymer couple could act as a universal switch for protein activity control.

Any substrate capable of having the polymeric surface may be used. The substrate may be a different material with a polymer coating, or it may be a solid substrate of the polymeric material.

The polymeric surface can comprise poly(2-hydroxymethyl thieno[3,4-b]-1,4-dioxane). The structure of the monomer and the two conductive states of the polymer are shown below. The doped form of the polymer on the right-hand side of the equation is relatively conductive, while the dedoped form on the right is less conductive. A relatively small voltage is required to change the conductivity state of this polymer, which in many cases avoids causing a redox reaction in the enzyme. This monomer is derived from EDOT. Polymers made from EDOT and other derivatives of EDOT may be possible, as well as combinations of more than one polymer, including EDOT-based polymers and/or other polymers.

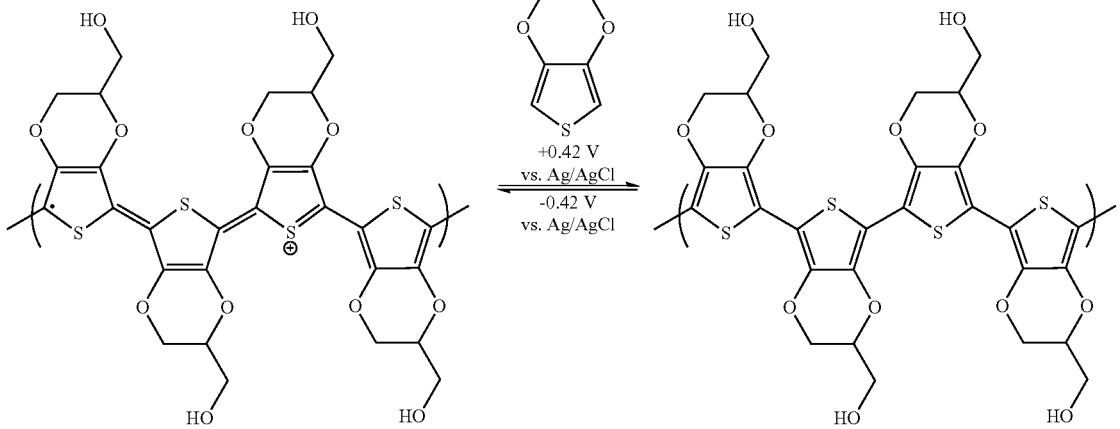

Figure 2:
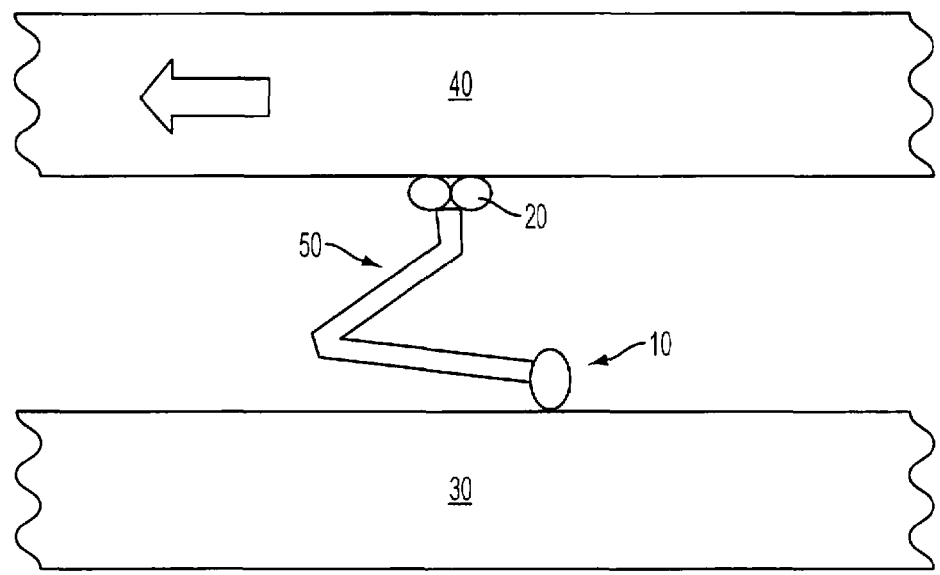
FIG. 2 schematically illustrates kinesin bound to a substrate and a microtubule.

Suitable enzymes include, but are not limited to, hydrolases such as kinesins, β-galactosidases, lysozymes, and combinations thereof. More than one different enzyme may be used. Hydrolases may have an advantage in that the activity level is more easily measured. Kinesin is of interest because it can bind to a microtubule, such as a microtubule of a polymer of tubulin. When adenosine triphosphate (ATP) is available to kinesin, it has a motor activity that moves the microtubule. This is schematically illustrated in FIG. 2. Kinesin 10 is bound to the substrate 20 at its cargo-binding and regulatory domain 30, and to the microtubule 40 at its microtubule-binding domain 50. The kinesin motor pushes the microtubule 8 nm horizontally per each ATP hydrolyzed to ADP+$PO_4^-$. Kinesin (120 kdal) is highly flexible and can attain a fully extended (linear) conformation. The microtubule is composed of αβ-tubulin (120 kDal) repeat units.

A sensor may be made by exposing the substrate with kinesin and microtubules to a sample and allowing the microtubule to adsorb an analyte in the sample. Subsequently, the conductivity may be changed so that the microtubules begin moving towards a detector.

Appropriate chemical derivitization of the conducting polymer, or possibly the kinesin itself, may allow the kinesin activity to be (reversibly) lowered to levels very near zero.

It may be that kinesin from *Drosophila* sp. is susceptible to surface effects because it has an unusually high aspect ratio, and is highly flexible and allosteric. It is possible to create hybrid proteins via genetic engineering, and one can envision forming a family where all members have the above features of kinesin but each has different function. The activities of the entire family could then be controlled using the conducting polymer substrate.

Without limiting the claims to any particular mechanism, it is believed that the conformation of the enzyme may be changed by a change in the conductivity of the polymeric surface. This change in conformation can in turn change the activity of the enzyme. The effect of this is that the enzyme may be made more or less active by applying the appropriate positive or negative bias to the polymer. This switching function may be completely reversible for an indefinite number of cycles. In the case of kinesin and tubulin, the microtubule may move a different speed depending on the voltage that was applied to the polymer.

The cationic doped conducting polymer may exert its effect on K401-BCCP-His6 through its tail domain, which is known to be an inhibitory regulator of the motor domain. The tail sequence 883-936 is highly positively charged, with eight excess positive charges from lysine and arginine residues. It is theorized that the doped form of the conducting polymer causes this segment in K401-BCCP-His6 to experience an electrostatic repulsion from the surface, and an upward migration that enables it to exert its inhibitory action at or near the motor domain. When the polymer is dedoped, the segment may then re-adsorb to the neutral surface.

Under standard conditions, the tail domain of kinesin is known to be a noncompetitive inhibitor of the motor domain, i.e. its influence causes a reduction in $k_{cat}$ while $K_m$ remains constant. The tail acts both on free kinesin and on kinesin with ATP or ADP bound. In the presence of the doped conducting polymer surface, the tail appears to act as an uncompetitive inhibitor—its influence causes a reduction in both $k_{cat}$ and $K_m$, and it acts on kinesin only when ATP or ADP is bound in the motor domain.

Figure 7:
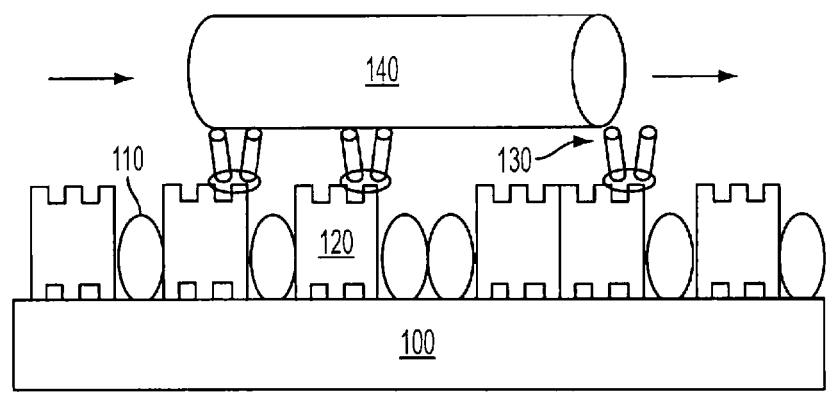
FIG. 7 schematically illustrates the streptavidin-BSA-kinesin system.

An additional compound may be placed on the polymeric surface with the enzyme bound to the compound. An example suitable compound is streptavidin. More than one such compound may be used, and the polymeric surface may be only partially covered with the compound. For example, bovine serum albumin (BSA) may also be on the polymeric surface without having enzyme bound to it. This is schematically illustrated in FIG. 7 showing the substrate 100, BSA 110, streptavidin 120, kinesin 130, and microtubule 140. Without limiting the claims to any particular mechanism, it is believed that the conformation of the streptavidin may be changed by a change in the conductivity of the polymeric surface. The enzyme may or may not change conformations in this situation, however, the orientation of the enzyme may be changed be the streptavidin conformation change. Since the enzyme is bound to a substrate, a change in orientation can lead to a change in the activity level.

The switching activity may also be used to control the activity of a second enzyme that is not bound to the substrate, such as an enzyme that catalyzes a reaction with adenosine diphosphate (ADP). The bound enzyme may produce ADP at different rates depending on the doping state, thus controlling the supply of ADP to the second enzyme. When less ADP is available, the activity of the second enzyme may be lower than when more ADP is available.

Having described the invention, the following examples are given to illustrate specific applications of the invention. These specific examples are not intended to limit the scope of the invention described in this application.

Example 1

Synthesis of Poly(OH-EDOT) Films

The monomer, iron p-toluenesulfonate, and imidazole moderator were used in an overall 30% concentration in butanol, in a molar ratio of 2:2:1. The solution was spin-cast on PET plastic films using speeds in the range 1500 to 4000 RPM, forming an adherent conducting layer with electrical surface resistances ranging from 210 Ω/sq to 430 Ω/sq (doped form) and 1200 Ω/sq to 1420 Ω/sq (dedoped form).

Example 2

Immobilization of Proteins

The protein ensemble (streptavidin, BSA, *Drosophila* kinesin K401-biotin carboxyl carrier protein (BCCP)-His6 and MTs) was deposited onto the conducting polymer surface (initially doped) using standard flow or droplet deposition methods. Flow cells were assembled using double-sided tape as a spacer creating a channel of approximate dimensions 5 mm×10 mm×0.04 mm. For the non-electrochemical assays, the poly(OH-EDOT)/PET substrate was placed on a glass slide with the conducting polymer layer down. The proteins were introduced using the standard capillary-flow technique. The buffer for all experiments was BRB80 (80 mM Pipes, 2 mM $MgCl_2$, 1 mM EGTA, pH 6.95 with KOH). The flow cells were sequentially filled with a streptavidin solution (*Streptomyces avidinii*, Sigma-Aldrich, 1.0 mg/mL in BRB80, 10 min deposition time), BSA solution (Sigma-Aldrich, 1.0 mg/mL in BRB80, 10 min deposition time), standard kinesin solution (40 μg/mL kinesin K401-BCCP-His6 with 1 mM ATP in BRB80, 10 min deposition time), and finally a motility buffer with rhodamine-labeled microtubules (1-10 μm in length), containing 1 mM ATP and stabilized with 10 μM Taxol with oxygen scavenging additives (20 mM D-glucose, 20 μg/mL glucose oxidase, 8 μg/mL catalase, 0.2% 2-mercaptoethanol). Flow cells were sealed with immersion oil to prevent evaporation. The assays were performed at room temperature (21° C.).

Example 3

Activity Assay

The activity was measured both directly and indirectly. In the direct assay, the ATP consumption rate was determined by measuring the time-dependent levels of free phosphate ion in solution. A poly(OH-EDOT) substrate with kinesin and an ITO counter electrode were placed in a motility buffer and connected to a power supply. A chromophore (lambda max 360 nm) is released via an enzyme-catalyzed nucleophilic displacement. KinesinATPase activity was measured via $PO_4^{2-}$ detection using an enzyme-liked (purine nucleoside phosphorylase, PNP) assay (Webb, Proc. Natl. Acad. Sci. 19989, 4884). PNP kit and methylanthranyl-ADP (MANT-ADP) were purchased from Pierce (Rockford, Ill.). MANT-ADP fluorescence measurements were made using SpectrofluorPlus fluorimeter (Tecan, Research Triangle Park, N.C.).

When the polymer substrate was in the doped state, the steady-state phosphate release rate was 0.000405 AU/min. The surface was then electrochemically transformed to the dedoped state by applying an electrical bias of +1.0 volt for 2 minutes. After the voltage application, the circuit was shut off. When the polymer was in the dedoped state, the steady-state kinesin phosphate release rate was 0.000626 AU/min. The ratio of release rates (dedoped vs. doped surface) is therefore 1.55. These results are shown in FIG. 1.

Figure 3:
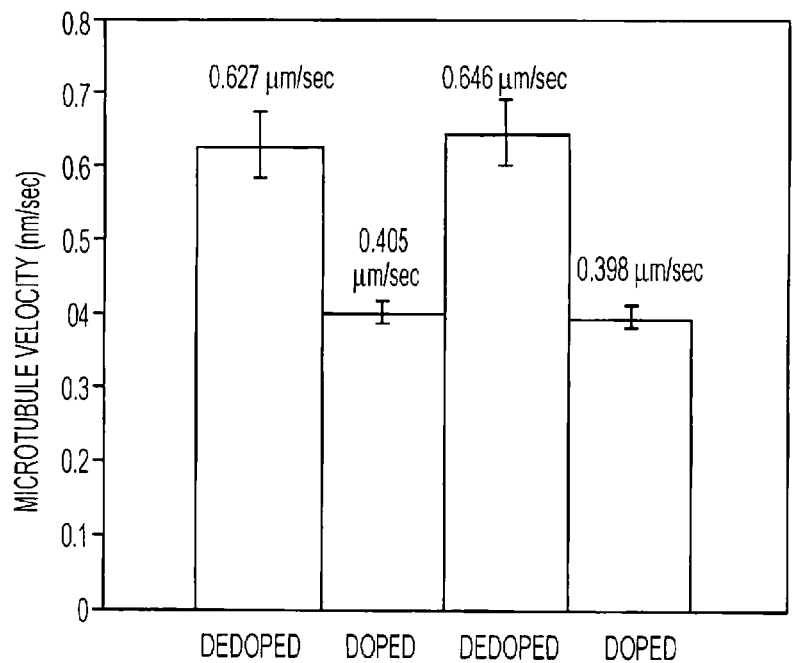
FIG. 3 shows a plot of microtubule speeds for both doped and dedoped substrates.

It has recently been well established that as kinesin hydrolyzes a single ATP molecule, it induces an eight-nanometer movement of a microtubule. Therefore enzyme activity can be indirectly assayed by simply determining the average speed of a large population of microtubules. This was done using fluorescently-labeled microtubules, and their gliding speeds were then carefully measured using confocal microscopy. Microtubules were visualized on the conducting polymer using an Olympus Opelco BX51 fluorescence microscope and their speeds quantified using Metamorph image analysis software (Universal Imaging, Downingtown, Pa.). This assay method was then combined with a transparent electrochemical cell containing a poly(OH-EDOT) support. The poly(OH-EDOT) was ~80% transparent in the visible range, allowing the microtubules to be easily seen and their speeds measured. The surface was initially in the dedoped state, and the average microtubule speed was found to be 0.63 µm/sec. The surface was then electrochemically doped by applying a bias of −1.0 volt for 1 minute. The average microtubule speed was measured and found to be 0.40 µm/sec. The resulting ratio in speed differences (dedoped vs. doped surfaces) is 1.55, a striking exact correlation with the ATP hydrolysis ratios on the two surfaces. The surface was then cycled between the two states once more to give an overall cycling history of −1.0 V, +1.0 V, −1.0 V, +1.0 V with corresponding polymer states dedoped, doped, dedoped, doped (FIG. 3). For the second doping cycle the microtubule speeds were 0.63 (dedoped) and 0.40 (doped), giving a speed difference ratio of 1.62. This experiment demonstrated that 1) the speeds and thus kinesin activity could be reversibly controlled by changing the doping state of the conducting polymer surface, 2) the differences in microtubule speeds were directly due to alterations of the kinesin activity vs. another artifact such as preferential heating of one surface state vs. the other by the confocal microscope laser, and 3) the surface does not cause a decrease in enzyme chemomechanical efficiency—the microtubule gliding speeds in the experiments remain tightly coupled with kinesin ATP hydrolysis rates.

It was first suggested that the slowing of the microtubules on the doped surface may be due to direct electrostatic attraction between the surface and the tubule protein. However, electrophoretic measurements on the tubules show that each 120 kD αβ-tubulin dimer (the constituent protein) has a net charge of only −0.19 esu (Stracke et al., "Analysis of the migration behavior of single microtubules in electric fields", *Biochem. Biophys. Res. Comm.*, 293, 602 (2002)). This tiny amount of net charge is not expected to be enough to provide a mechanism for microtubule speed control via interactions with the positively charged, doped polymer surface. Also, a Michaelis-Menten kinetic analysis of the kinesin (see below) indicates that this direct interaction is not the cause of the observed speed differences.

It is curious that virtually no speed differential is observed if ordinary PEDOT or glass is used as substrate instead of the poly(OH-EDOT). This suggests that the hydroxyl group of the latter becomes H-bonded to the kinesin, bringing regions of the protein nearer to the surface in a manner that allows greater interaction with the polymer when it is in its charged form.

Example 4

Control Experiments

A few very important control experiments were performed. In the first, the poly(OH-EDOT) was dedoped chemically instead of electrochemically (immersion in 2.0 M ammonium hydroxide for 5 minutes, and rinsing thoroughly). The proteins were added to the surface afterwards. When the microtubule speeds on the dedoped surface were measured and compared to the doped surfaces, they were found to be faster by a factor of 1.39 (vs. 1.62 above). The fact that that a speed differential was observed when chemical dedoping was used shows that the speed differences originate from differences in the physical state of the surface (charged vs. neutral) rather than from electrochemical effects on the media or protein that might occur when the 1.0 volt bias is applied (electrolysis of water, electrochemically-induced redox changes in the protein). This also demonstrates that electrochemical dedoping may be more thorough than the chemical method.

Another concern was that the doped conducting polymer surface may cause a local (nanoscale) drop, or rise, in pH leading to differences in kinesin activity (the pH optimum for kinesin is in the range 6.7-7.8). This appears unlikely because of two points made in the literature—1) the conductivity of doped PEDOT is known to have virtually no pH sensitivity (Mercedes et al., "Influence of oxygen and carbon dioxide on the electrochemical stability of poly(3,4-ethylenedioxythiophene) used as ion-to-electron transducer in all-solid-state ion-selective electrodes", *Sensors and Actuators B*, 82, 7-13 (2002)). It follows that the polymer probably does not affect the pH in its local aqueous surroundings. Even if it did, the process would have to be catalytic and not require actual consumption of the polarons—their effective concentration is only 3 mM (see below), and the buffering effect of the 50 mM PIPES would maintain the local pH at 7.0. Assuming a catalytic lowering of pH, one could envision coordination of a water molecule to a polaron (cation) in a manner that permits abstraction of a proton from the water, generating OH, and raising the local pH. But MT speeds (thus kinesin activity) are known to be practically invariant up to pH 7.8 (Bohm et al., "Speeding Up Kinesin-Driven Microtubule Gliding In Vitro by Variation of Cofactor Composition and Physicochemical Parameters", *Cell Biol. Int.*, 24, 335 (2000)). Finally, microtubule speed differentials arise only with poly(OH-EDOT) and not with underivatized PEDOT. If the doped form of the polymer was in fact raising (or lowering) the local pH and influencing microtubule speeds, the underivatized polymer should cause a speed differential also.

Figure 4:
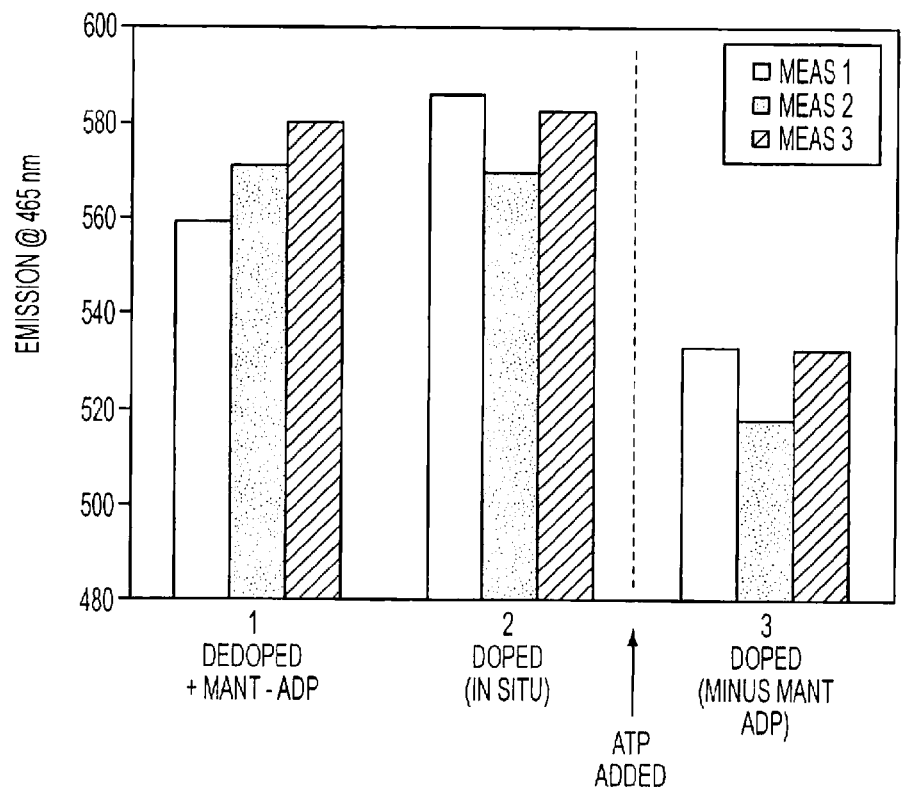
FIG. 4 shows a plot verifying that the number of microtubules bound to the substrate is not affected by the doping state.

A second key control experiment was undertaken to verify that the changes in the doping state of the surface were not simply causing partial absorption/desorption of kinesin molecules from the surface, with the microtubule speeds then determined by the number of kinesin motors available. To measure the number of kinesin molecules on the surface, a fluorescent ATP analogue (methylanthraninoyl-ADP (MANT-ADP)) that binds tightly to the kinesin ATP-binding site was used. A transparent electrochemical cell containing the poly(OH-EDOT) support was constructed and the kinesin and microtubules were added. Buffer containing MANT-ADP was added, the cell was rinsed thoroughly, and the fluorescence was measured (in this assay the amount of fluorescence @465 nm correlates directly with the number of kinesin molecules on the surface). The doping state of the surface was then changed electrochemically, the cell was rinsed, and the fluorescence was measured again. The level did not change between the two doping states (FIG. 4), indicating that the number of kinesin molecules on the surface stayed the same in both doping states. Addition of ATP causes the MANT-ADP to be displaced, and the surface fluorescence was reduced to the background level.

Example 5

Kinetics

At this point it was clear that the polymer surface was exerting a direct, reversible effect on the kinesin protein itself. The nature of this influence was examined by treating the charged species in the doped polymer form (the radical cation, or polaron) as an inhibitor, and quantified the enzyme kinetics in terms of Michaelis-Menten parameters. First, the surface concentration of the polarons was calculated using the established value of one polaron per four polymer repeat units for fully doped thiophene-type polymers. Using a polymer film volume of 1 cm×1 cm×1 Angstrom, the polaron surface concentration was found to be $1.17 \times 10^{-11}$ moles polarons/$cm^2$. If one then encloses a kinesin molecule in a cube 30 nm per side and considers the polarons on the 30 nm×30 nm surface region to be distributed in the cube volume, an apparent local polaron concentration ($[I_{app}]$) of 3.89 mM is obtained.

Figure 5:
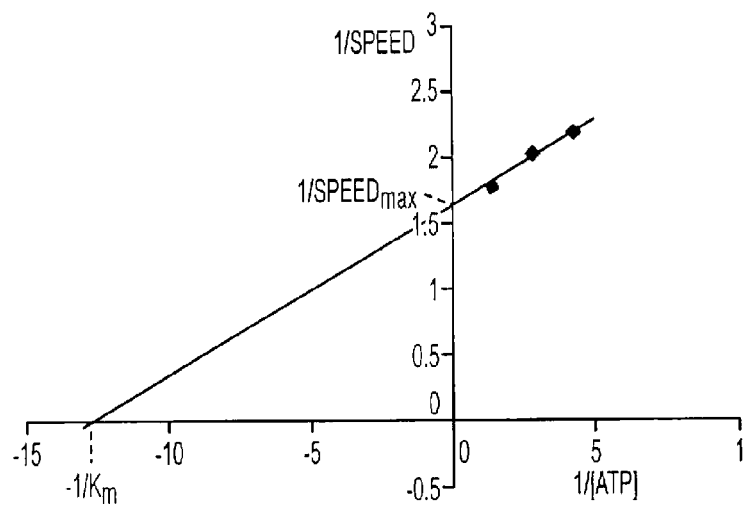
FIG. 5 shows a kinetic model of the kinesin-microtubule system.

The Michaelis-Menten analysis assumes a kinetic model of the type shown in FIG. 5 (E=enzyme, ES=enzyme-substrate complex, P=product, $k_{cat}$=catalytic turnover rate constant, $D_{step}$=8 nm, $K_m$=Michaelis constant). The kinetics of most enzymes, including kinesin, is accurately described with this model. Since reaction rate and microtubule speed are coupled through the established 8 nm step per ATP molecule hydrolyzed, the enzyme ATP hydrolysis rate can be expressed in terms of average observed microtubule speeds. The reciprocal of speed is plotted vs. the reciprocal of ATP concentration, and the maximum attainable speed (at infinite substrate concentration) is represented graphically as the reciprocal of the y-intercept. The ATP concentration that results in a speed of one-half of the maximum is termed the Michaelis constant ($K_m$) and is represented as the (−) reciprocal of the x-intercept. Determination of $Speed_{max}$ allows the catalytic turnover rate constant ($k_{cat}$) of the enzyme to be quantified. The Michaelis constant can also be viewed as a measure of how strongly an enzyme binds its substrate, with lower values indicating higher affinity.

Figure 6:
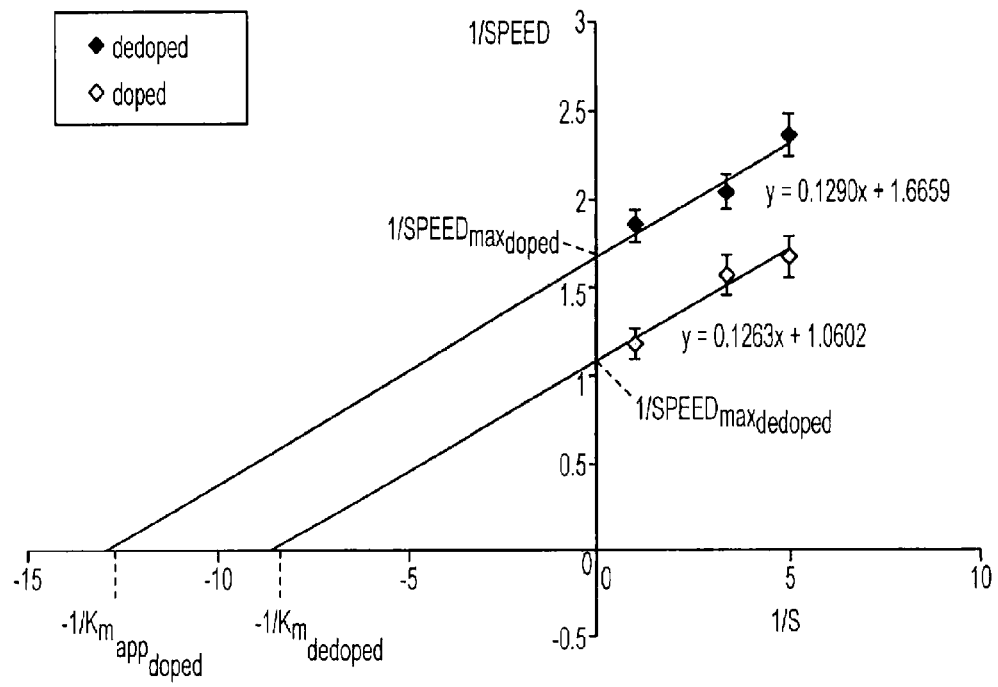
FIG. 6 shows a plot comparing the kinetics of the kinesin-microtubule system for both doped and dedoped substrates.

If a Michaelis plot is constructed in the presence of an enzyme inhibitor, and compared to one constructed without inhibitor, graphical differences in the plots can quickly reveal the mode of action of the inhibitor. This analytical method was applied to this system (FIG. 6), treating the polarons of the doped polymer as the inhibitor. The lower set of points and their regression correspond to the microtubule speed on the dedoped surface; the upper set, the doped surface. The strikingly parallel relationship of the two regressions is a direct indication that the polarons act as an "uncompetitive" inhibitor (terminology from classical enzymology). With this type of inhibition, the inhibitor acts only on the enzyme-substrate complex, not on the free enzyme, and not on the substrate (Scheme 1). The inhibition constant $K_{i\ app}$ represents the concentration of inhibitor necessary to reduce Speedmax by 50%. In terms of this system, the surface polarons evidently exert their inhibitory effect on the kinesin when it has either ATP or its hydrolysis product ADP bound. They have no effect on free kinesin or on the ATP (Scheme 2. Scheme 1 represented in terms of the kinesin-microtubulin system, where the polarons I act as an uncompetitive inhibitor. The inhibition constant $K_{i\ app}$ is expressed as "apparent" because it is not known which ES complex (MT-K-ATP or MT-K-ADP-$PO_4^-$, or both) is acted upon by the polarons. (MT=microtubule, K=kinesin.). This suggests that kinesin undergoes a conformation change upon substrate binding that makes it susceptible to influences from the conducting polymer support, such as ion-pairing (doped polymer state) or hydrophobic interactions (dedoped polymer state). These conformation changes affect the catalytic activity of the enzyme and thus affect the microtubule speeds.

Scheme 1

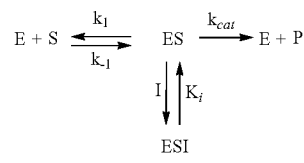

ESI

Scheme 2

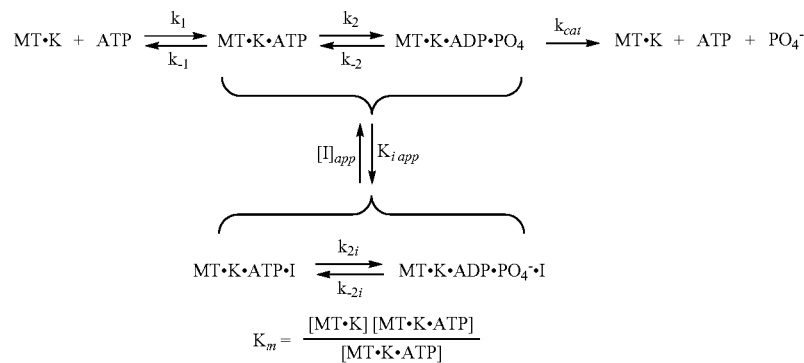

Further graphical inspection allows extraction of the full set of kinetic parameters for each surface state: $\text{Speed}_{max\ doped}$, $\text{Speed}_{max\ dedoped}$, $K_{m\ app\ doped}$, $K_{m\ dedoped}$, $k_{cat\ doped}$, and $k_{cat\ dedoped}$. (The subscript "app" denotes apparent, i.e., measured in the presence of both inhibitor and substrate). The inhibition constant $K_{i\ app}$ was also determined for the doped surface. These values are listed in Table 1. It is of interest that $K_{m\ app\ doped}$ is ca. 35% lower than $K_{m\ dedoped}$, indicating that the kinesin on the doped surface has a markedly increased affinity for ATP. However, $k_{cat\ doped}$ is ca. 36% lower than $k_{cat\ dedoped}$. The fact that an increased affinity for substrate is accompanied by a decreased catalytic turnover rate suggests that either 1) the polarons (doped surface) induce a conformational change across the entire ATP binding pocket, including the region containing the catalytic amino acid residues and the activated water molecule used for the ATP hydrolysis or 2) it causes a conformational change only in the region containing the catalytic residues, and an allosteric response by the protein causes it to increase its affinity for ATP. The latter mechanism may be the most likely, since it is consistent with the known allosteric nature of the protein, and it may represent an evolutionary adaptation of the protein wherein it "primes" its fuel supply when faced with an inhibitor.

The inhibition constant $K_{i\ app}$ was found to be 6.80 mM, indicating that the polarons are relatively weak in their action as an uncompetitive inhibitor. Values for other inhibitors range from 48 μM (ADP) to 9.3 mM ($PO_4^{2-}$).

TABLE 1

| constant | value |
| --- | --- |
| $\text{Speed}_{max\ doped}$ | 0.600 μm/s ± 0.03 |
| $\text{Speed}_{max\ dedoped}$ | 0.943 μm/s ± 0.05 |
| $K_{m\ app\ doped}$ | 0.0775 mM ± 0.004 |
| $K_{m\ app\ dedoped}$ | 0.119 mM ± 0.006 |
| $[I]_{app}$ | 3.89 mM |
| $k_{cat\ doped}$ | 75.0 sec$^{-1}$ ± 3 |
| $k_{cat\ dedoped}$ | 118 sec$^{-1}$ ± 6 |
| $K_{i\ app}$ | 6.80 mM ± 0.3 |

Example 6

Other Enzymes

Figure 8:
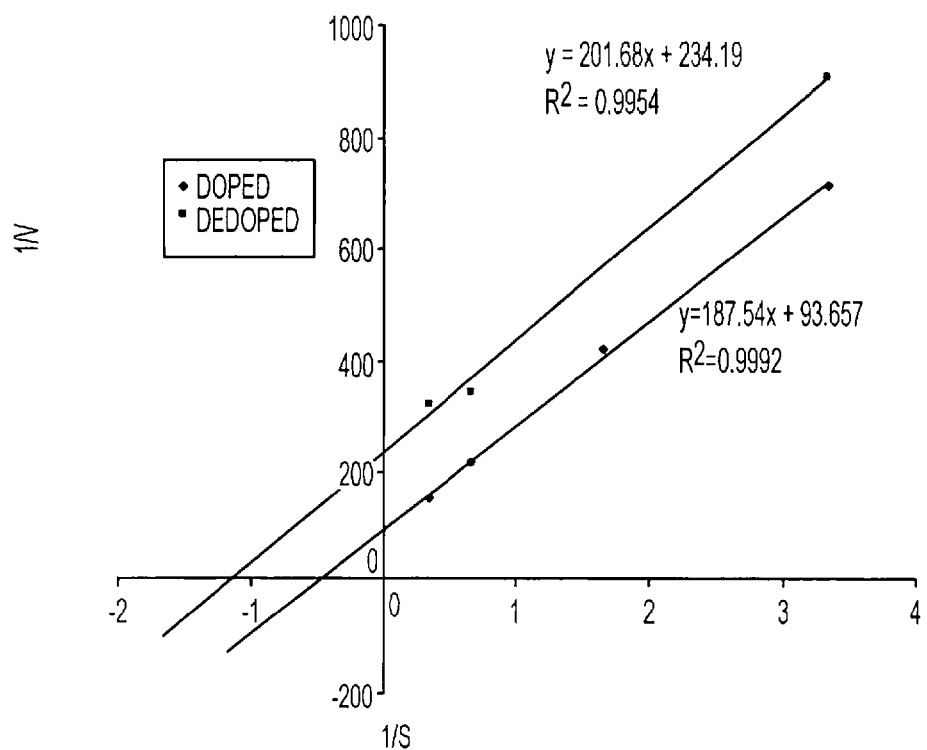
FIG. 8 shows a plot comparing the kinetics of the β-galactosidase system for both doped and dedoped substrates.
Figure 9:
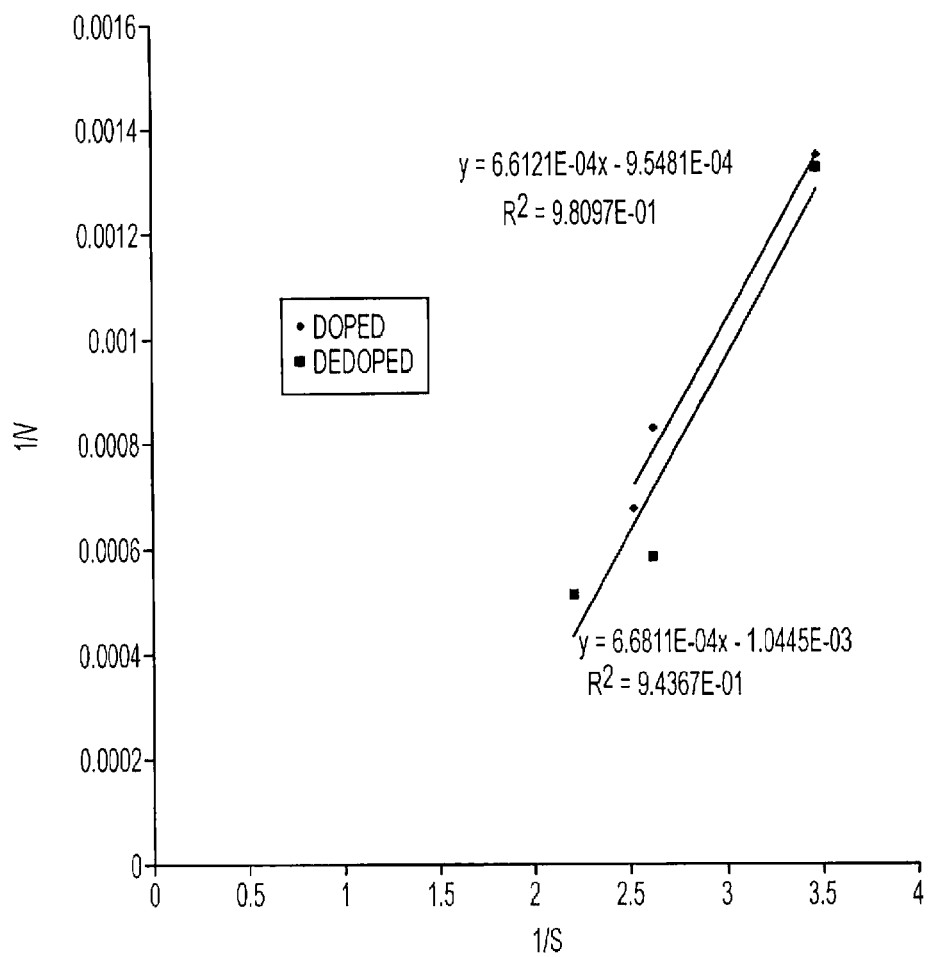
FIG. 9 shows a plot comparing the kinetics of the lysine system for both doped and dedoped substrates.

FIGS. 8 and 9 show the Michaelis plots for Bgal-biot-Str on CP and for Lysozyme-biotin-streptavidin on poly(OH-EDOT) respectively. β-Galactosidase has a MW of about 500,000 and has 4 tetramers in 222 symmetry. Lysozyme has a MW of about 10,000 and is a hard, charged sphere. In contrast, kinesin has a MW of about 60,000 and is flexible. All three show the same uncompetitive inhibitor kinetics.

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A device comprising:
   a substrate comprising poly(2-hydroxymethyl thieno[3,4-b]-1,4-dioxane);
   a streptavidin non-covalently adsorbed onto the poly(2-hydroxymethyl thieno[3,4-b]-1,4-dioxane); and
   kinesin-biotin carboxyl carrier protein non-covalently bound to the streptavidin.

2. The device of claim 1, wherein the device further comprises:
   a microtubule bound to the kinesin.

3. The device of claim 2, wherein the microtubule is a polymer of tubulin.

4. The device of claim 1, further comprising:
   adenosine triphosphate that is available to the kinesin.

5. The device of claim 4, further comprising:
   an enzyme that catalyzes a reaction with adenosine diphosphate.

6. A method of controlling enzyme activity comprising:
   providing a substrate comprising poly(2-hydroxymethyl thieno[3,4-b]-1,4-dioxane);
   non-covalently adsorbing streptavidin onto the poly(2-hydroxymethyl thieno[3,4-b]-1,4-dioxane);
   non-covalently binding kinesin-biotin carboxyl carrier protein to the streptavidin; and
   applying a voltage to the poly(2-hydroxymethyl thieno[3,4-b]-1,4-dioxane) that changes the poly(2-hydroxymethyl thieno[3,4-b]-1,4-dioxane) from a doped form to a dedoped form.

7. The method of claim 6, wherein the method further comprises:
   binding a microtubule to the kinesin.

8. The method of claim 7, wherein the microtubule is a polymer of tubulin.

9. The method of claim 6, further comprising:
   providing adenosine triphosphate to the kinesin.

10. The method of claim 9, further comprising:
    providing an enzyme that catalyzes a reaction with adenosine diphosphate.

11. The method of claim 6, further comprising:
    reverting the poly(2-hydroxymethyl thieno[3,4-b]-1,4-dioxane) to the doped form.

* * * * *